United States Patent [19]
Disch et al.

[11] Patent Number: 5,234,832
[45] Date of Patent: * Aug. 10, 1993

[54] PROCESS FOR CLEANING AND DISINFECTING HEAT AND CORROSION SENSITIVE MEDICAL INSTRUMENTS

[75] Inventors: Karlheinz Disch, Haan; Klaus Hachmann, Hilden; Klaus Bansemir, Langenfeld, all of Fed. Rep. of Germany

[73] Assignee: Henkel Kommanditgesellschaft auf Aktien, Duesseldorf, Fed. Rep. of Germany

[*] Notice: The portion of the term of this patent subsequent to Nov. 15, 2005 has been disclaimed.

[21] Appl. No.: 353,291

[22] Filed: May 17, 1989

[30] Foreign Application Priority Data

May 17, 1988 [DE] Fed. Rep. of Germany ....... 3816734

[51] Int. Cl.$^5$ .................. A01N 00/00; C11D 3/48; C11D 17/00; B01F 17/30
[52] U.S. Cl. ...................... 435/264; 422/36; 252/106; 252/173; 252/174.12; 252/174.21; 252/DIG. 14; 252/357
[58] Field of Search ............. 435/264; 252/174.12, 252/106, 173, 174.21, DIG. 14, 357; 422/36

[56] References Cited

U.S. PATENT DOCUMENTS

| | | | |
|---|---|---|---|
| 3,697,222 | 10/1972 | Sierra | 21/54 A |
| 4,456,544 | 6/1984 | Lupova et al. | 435/264 |
| 4,511,490 | 4/1985 | Stanislowski et al. | 435/264 |
| 4,784,790 | 11/1988 | Disch et al. | 514/693 |
| 4,801,451 | 1/1989 | Hellgren et al. | 435/264 |
| 4,867,797 | 9/1989 | Thomasen et al. | 435/264 |
| 4,876,024 | 10/1989 | Enomoto et al. | 435/264 |
| 4,994,200 | 2/1991 | Disch et al. | 252/106 |
| 4,996,146 | 2/1991 | Kessler | 435/264 |

FOREIGN PATENT DOCUMENTS

| | | |
|---|---|---|
| 118933 | 9/1984 | European Pat. Off. . |
| 268227 | 5/1988 | European Pat. Off. . |
| 0342499 | 11/1989 | European Pat. Off. ............ 435/264 |
| 3327466 | 2/1988 | Fed. Rep. of Germany . |
| 434574 | 10/1967 | Switzerland . |

OTHER PUBLICATIONS

Handbook of Chemistry & Physics, 43rd edt., p. 1747, 1962.

*Primary Examiner*—Douglas W. Robinson
*Assistant Examiner*—Deborah K. Ware
*Attorney, Agent, or Firm*—Ernest G. Szoke; Wayne C. Jaeschke; Daniel S. Ortiz

[57] ABSTRACT

The invention is a process for cleaning and disinfection of heat and corrosion sensitive medical instruments, particularly endoscopes in which the surfaces of the medical instruments are contacted with a detergent and disinfectant solution. The solution has a pH of from 6 to 8 and contains a low foaming nonionic surfactant, a proteolytic enzyme, a complexing agent, and an aldehyde selected from the group consisting of formaldehyde and aliphatic dialdehydes containing 2 to 8 carbon atoms and, optionally, other standard detergent and disinfectant constituents. The cleaning solution is heated to 55° to 65° C. and kept at that temperature for 1 to 15 minutes during contact with the surfaces of a medical instrument. The surfaces are rinsed at least twice with water, the water being heated to 55° to 65° C. at least in the last rinse cycle and the medical instruments are dried with sterilized hot air at a temperature of 40° to 60° C. Water having a hardness of 3° to 8° Gh is used.

12 Claims, No Drawings

PROCESS FOR CLEANING AND DISINFECTING HEAT AND CORROSION SENSITIVE MEDICAL INSTRUMENTS

BACKGROUND OF THE INVENTION

1. Field of the Invention

In medical diagnosis and therapy, surgical operations are being replaced to an increasing extent by the use of endoscopes. This development has been made possible by the development of flexible glass fiber endoscopes. In the course of their intended use, the endoscopes become massively infected with microorganisms which are present in body cavities, on the mucous membrane and in the blood. Accordingly, endoscopes have to be thoroughly cleaned and disinfected after each use.

Glass fiber endoscopes are complex precision instruments which have moving parts and are made from a number of different materials. Because of their construction and diversity of materials, glass fiber endoscopes are extremely difficult to clean and disinfect. The outer surfaces of the instrument and also the narrow bores, present in the interior of the instrument, have to be cleaned and disinfected. In view of the sensitivity of the materials of which the instrument is made, cleaning and disinfection have to be performed in such a way that no residues of the cleaning and disinfecting preparations remain on the treated surfaces of the instrument. The process of thermal sterilization normally used for medical instruments cannot be applied to endoscopes because endoscopes are made partly of temperature sensitive materials. Another factor to be taken into consideration is that many of the metal parts present are susceptible to corrosion. Finally, endoscopes must be cleaned and disinfected in a short time so that they are always ready for the treatment of the next patient.

Only in recent years have manufacturers of glass fiber endoscopes succeeded in developing instruments which may be completely immersed in cleaning and disinfection baths and which are capable of withstanding temperatures of up to 70° C. without damage. Comparable results have been obtained with a number of other medical instruments which are also made of temperature sensitive and/or corrosion sensitive materials.

2. Statement of Related Art

DE-PS 33 27 466 describes a process for cleaning utilitarian medical and patient care articles in which the articles are treated with a standard detergent in a carrier liquid (water) in a closed system at temperatures of at most 70° C. A disinfectant is then additionally introduced into the carrier liquid. The disinfectant used is a mixture of glutaraldehyde and/or succinic acid dialdehyde with a salicylate and a polyethylene glycol. In the practical application of the process, separate temperature holding times are provided for the cleaning treatment and the disinfecting treatment. Alkaline detergent compositions are recommended for the cleaning treatment. This process has proved to be unsuitable for the cleaning and disinfection of endoscopes, because it leads to corrosion phenomena on the metal parts of the endoscopes after only a limited number of process cycles.

The object of the present invention is to develop a process which, through a combination of thermal and chemical treatments, enables heat and corrosion sensitive medical instruments, particularly endoscopes, to be reliably cleaned and disinfected in a short time and which does not damage the treated instruments, even in the event of long-term application. This process is designed in such a way that it may optionally be carried out in an automatic washing machine. In addition, the spent cleaning and disinfecting solutions are sterile so that they may safely be added to the normal wastewater. This object is achieved by the process described hereinafter.

BRIEF DESCRIPTION OF THE INVENTION

Other than in the operating examples and claims, or where otherwise indicated, all numbers expressing quantities of ingredients or reaction conditions used herein are to be understood as modified in all instances by the term "about".

The present invention relates to a process for the cleaning and disinfection of heat and corrosion sensitive medical instruments, particularly endoscopes, using aqueous cleaning and disinfectant solutions which comprises:

a) contacting the surfaces to be treated with a detergent and disinfectant solution which contains:
   at least one low foaming nonionic surfactant;
   at least one proteolytic enzyme;
   at least one complexing agent;
   at least one aldehyde from the group consisting of formaldehyde and aliphatic dialdehydes containing 2 to 8 carbon atoms; and
   optionally other standard detergent and disinfectant constituents at a pH of from 6 to 8, the cleaning solution is heated to 55° to 65° C., kept at that temperature for 1 to 15 minutes and then drained off:

b) rinsing the surfaces treated at least twice with water, at a temperature of 55° to 65° C. at least in the last rinse cycle; and c) drying the treated surfaces with sterilized hot air at 40° to 60° C.

Water having a hardness of 3° to 8° Gh (German hardness) being used in steps a) and b).

It is preferred to use a detergent and disinfectant solution containing:
   from 0.1 to 1.0 g/liter low foaming surfactant;
   from 0.03 to 0.3 AU/liter proteolytic enzyme (AU-=Anson Units);
   from 0.02 to 0.3 g/liter complexing agent; and
   from 0.5 to 5 g/liter aldehyde in step a).

DETAILED DESCRIPTION OF THE INVENTION

Low foaming nonionic surfactants suitable for use in the detergent and disinfectant solution of step a) are, preferably alkylene oxide adducts obtained by addition of from 3 to 30 mol ethylene oxide and/or propylene oxide to aliphatic alcohols containing from 2 to 6 hydroxyl groups and from 2 to 12 carbon atoms, to fatty alcohols, fatty acids, fatty amines or alkylphenols each containing from 8 to 18 carbon atoms (the terminal hydroxyl groups of these polyglycol ether derivatives can be etherified, esterified or acetylated). Particularly useful are adducts of from 3 to 15 mol ethylene oxide with saturated and unsaturated $C_8$-$C_{18}$ fatty alcohols, adducts of from 3 to 5 mol ethylene oxide and from 3 to 6 mol propylene oxide with saturated and unsaturated $C_8$-$C_{18}$ fatty alcohols (these mixed alkylene oxide adducts may be random or block polymers and also ether derivatives of the above-described fatty alcohol alkylene glycol ethers in which the terminal hydroxyl groups are etherified with a straight chain or branched chain saturated aliphatic $C_4$–$C_8$ alcohol). Particularly useful are polyethylene glycol ethers of the formula

$$R^1-O-(CH_2CH_2O)_n-R^2 \qquad (I)$$

in which $R^1$ is a straight chain or branched chain $C_8$–$C_{18}$ alkyl or alkenyl radical, $R^2$ is a straight chain or branched chain $C_4$–$C_8$ alkyl radical and n is a number of from 7 to 12, particularly preferred are polyethylene glycol ethers of formula I in which $R^1$ is a mixture of $C_{12}$–$C_{18}$ alkyl and/or alkenyl radicals comprising hydrogenated or nonhydrogenated tallow fatty alcohol and $R^2$ is an N-butyl radical while n is a number of from 9 to 10.

Particularly preferred proteolytic enzymes for the detergent and disinfectant solution of step a) are proteases obtained from bacterial strains. Suitable enzymes are, for example, the enzymes obtained from *Bacillus subtilis*, *Bacillus licheniformis* and *Streptomyces griseus*. Corresponding commercial preparations are available either in the form of solutions of the enzyme in a mixture of water and an organic solvent, for example 1,2-propanediol, or as solid granulates. These commercial forms generally contain water soluble calcium salts as potentiating and stabilizing agents. Solid preparations may be adjusted to a certain degree of activity by diluents, for example sodium sulfate, sodium chloride, alkali phosphate or alkali polyphosphate.

The cleaning solution of step a) can contain as complexing agents alkali metal salts of the following compounds nitrilotriacetic acid, ethylenediamine tetraacetic acid, 1-hydroxyethane-1,1-diphosphonic acid, aminotris-(methylenephosphonic acid), ethylenediamine tetrakis(methylenephosphonic acid), phosphonobutane tricarboxylic acid, tartaric acid, citric acid and gluconic acid. Alkali metal salts of phosphonobutane tricarboxylic acid being particularly preferred.

Examples of the preferred aliphatic $C_2$–$C_8$ dialdehydes present in the detergent and disinfectant solution of step a) are glyoxal, malonaldehyde, succinaldehyde and glutaraldehyde; glutaraldehyde is most preferred.

In principle, water having a hardness of from 3° to 8° Gh is used in the practical application of the process according to the invention. This applies both to the preparation of the cleaning and disinfectant solution and also to the wash cycles. The degrees of hardness mentioned above are best adjusted by passing tapwater at least partly over a cation exchanger which removes the cations responsible for hardness from the water. This cation exchange results in a displacement of pH value into the alkaline range. For this reason, the pH value of the detergent and disinfectant solution of step a) has to be adjusted to the range of pH 6 to pH 8.

For stability in storage, it has proved to be preferred to prepare separate detergent and disinfectant concentrates for the preparation of the detergent and disinfectant solution of step a). These concentrates may be formulated in such a way that they give solutions having a pH value in the required range on dilution with the tapwater treated with the cation exchanger. The water used for the wash cycles may optionally be adjusted with physiologically safe organic acids, for example with acetic acid, tartaric acid, lactic acid, malic acid, citric acid to a pH value in the range from pH 6 to pH 8 when the pH value of the softened water is significantly above 8.5.

During treatment in step a) of the process according to the invention, the endoscopes may be simultaneously exposed to the effect of ultrasound to enhance the cleaning and disinfecting effect.

Air sterilized before heating by passage through a microfilter is preferably used to dry the endoscopes in step d).

The spent detergent and disinfectant solution from step a) can be drained off into the wastewater without any further aftertreatment.

The process according to the invention can be carried out, for example, in closable, heatable stainless steel containers of appropriate dimensions which are provided with means for pumping the various liquids and the hot air used for drying through the endoscope bores to be cleaned. The containers are intended to comprise inlets and outlets for the cleaning and disinfecting solution and for the washing water and also for the hot air used to dry the instruments. It is of advantage if the endoscopes to be treated can be placed in a rack which fits in the stainless steel container. To carry out the individual steps of the process according to the invention, the container is charged with a quantity of liquid so that the endoscopes are fully immersed therein. The particular liquid present is continuously pumped at an adequate rate through the bores of the endoscope. When the treatment liquids are drained off, it is important to ensure that the liquid present in the bores is also removed.

Automatic washing machines of the type known and commonly used for the cleaning of laboratory instruments and medical instruments are particularly suitable for carrying out the process according to the invention. The machine should have the necessary attachments, for example means by which the liquids can be pumped through the bores of the endoscopes. In the automatic washing machine, the outer surfaces of the endoscopes are not brought into contact with the liquids by immersion therein, but instead by continuous spraying.

Stable, storable detergent and disinfectant concentrates which, in addition to the active ingredients can contain additional constituents of the type normally present in such concentrates are best prepared for use after dilution in step a).

An aqueous detergent concentrate for preparing the detergent and disinfectant solution used in step a) can contain, for example,
  from 5 to 10% by weight low foaming nonionic surfactant,
  from 7.1 to 77 AU/liter proteolytic enzyme,
  from 20 to 60% by weight enzyme stabilizer,
  from 1 to 5% by weight blending aid and
  from 0.05 to 0.5% by weight preservative.
The pH of the concentrate is adjusted to pH 4–6 with an acid, a base or an acid-base mixture.

Suitable enzyme stabilizers for the aqueous detergent concentrate are, for example, triethanolamine, morpholine, α-pyrrolidone, ethylene glycol, propylene glycol, glycerol, water-soluble calcium salts or mixtures of these compounds. Glycerol and/or propylene glycol is preferably used as the enzyme stabilizer.

Blending aids (solubilizers) suitable for the aqueous detergent concentrate are, for example, sodium cumenesulfonate, sodium toluenesulfonate, sodium xylenesulfonate, urea, polyethylene glycols, methyl acetamide and fatty alcohols, such as cetyl alcohol. Sodium cumenesulfonate is preferably used as the blending aid.

Detergent concentrates useful in the process of the present invention are susceptible to microbial infestation. Particularly, fungal growth is readily observed in the case of preservative-free compositions. For this reason, effective quantities of preservatives are added to the concentrates. Suitable preservatives are, for example, p-hydroxybenzoic acid methyl ester, 5-bromo-5-nitro-1,3-dioxane, glutaraldehyde, salicylic acid, 0-2-naphthyl-m-N-dimethylthiocarbanilate,5-chloro-5-methyl-4-isothiazolin-3-one, 2-methyl-4-isothiazolin-3-one, benzisothiazolin-3-one and mixtures of the last two compounds. p-Hydroxybenzoic acid methyl ester is preferably used as the preservative.

The foregoing description of the process according to the invention apply fully to the constituents present in the aqueous detergent concentrate, namely the low foaming nonionic surfactant and the proteolytic enzyme.

An aqueous disinfectant concentrate for use in step a) contains, from 10 to 40% by weight of an aldehyde from the group consisting of formaldehyde and aliphatic dialdehydes containing 2 to 8 carbon atoms,
from 0.5 to 2% by weight complexing agent and
from 7 to 15% by weight blending aid. The pH value of the concentrate is adjusted to pH 3–5 with an acid, a base or an acid-base mixture.

Particularly suitable blending aids for the disinfectant concentrate are lower aliphatic alcohols, such as ethanol, n-propanol and isopropanol and also ethylene glycol and triacetin. Ethanol is preferably used as the blending aid.

The foregoing description of the process according to the invention applies fully to the constituents present in the aqueous disinfectant concentrates, namely aliphatic dialdehyde and complexing agent.

EXAMPLE

Concentrates were prepared by mechanically blending the following individual constituents (pbw=parts by weight):

Detergent concentrate 8 pbw n-butyl ether of an adduct of 9.5 mol ethylene oxide with 1 mol hydrogenated tallow fatty alcohol (formula I: $R^1=C_{12-18}$ alkyl; $R^2=C_4$ alkyl; $n=9.5$)
1 pbw proteolytic enzyme (Alcalase ®, a product of Novo Industry A/S, Bagsvaerd, Denmark; 2.5 AU/g)
6 pbw glycerol
50 pbw 1,2-propylene glycol
2 pbw citric acid
3 pbw sodium cumenesulfonate
0.1 pbw p-hydroxybenzoic acid methyl ester ad 100 pbw water The mixture was adjusted to pH 5 with 37% by weight sodium hydroxide solution.

Disinfectant concentrate 20 pbw glutaraldehyde
1 pbw phosphonobutane tricarboxylic acid
8 pbw ethanol ad 100 pbw water The mixture was adjusted to pH 4 with 50% by weight sodium hydroxide solution.

The endoscopes were cleaned and disinfected in a closable, heatable stainless steel vessel (diameter approx. 60 cm; height approx. 65 cm) which was provided with inlets and outlets for the detergent and disinfectant solution, for the water used in the wash cycles and for the hot air used to dry the instruments. The apparatus was provided with a circulation pump by which the particular liquid present could be pumped through the bores of the fiber endoscope.

The tests were carried out with a standard commercial gastroscope.

Water adjusted by treatment with a cation exchanger to a hardness of 5° Gh was used to prepare the detergent and disinfectant solution. The same water was used to carry out the wash cycles after it was adjusted to pH 7 with lactic acid.

A ready-to-use detergent and disinfectant solution containing 0.45 g/liter surfactant, 0.06 g/liter enzyme, 2.4 g/liter glutaraldehyde and 0.12 g/liter phosphonobutane tricarboxylic acid was prepared by dilution of corresponding quantities of detergent concentrate and disinfectant concentrate.

The air used for drying was drawn through a microfilter and, before being introduced into the stainless steel vessel, was passed through a heating zone in which it was heated to 60° C.

To carry out the cleaning process, the endoscope was placed in the stainless steel container in a wire basket. The bores of the endoscope were connected to the circulation pump. In the individual steps of the process, water was delivered to the stainless steel container in such a quantity that the endoscope was completely immersed. During the individual steps of the process, the liquid present was continuously pump circulated through the bores of the endoscope.

After the stainless steel vessel had been filled with detergent and disinfectant solution, the detergent and disinfectant solution was heated to 60° C. and kept at that temperature for 10 minutes. After the detergent and disinfectant solution had been drained off, the endoscope was washed twice with cold water. The stainless steel vessel was then refilled with water which was heated to 60° C. and then drained off. Finally, sterile hot air was introduced for 5 minutes to dry the endoscope.

To test the disinfecting effect obtained in the process according to the invention, the bores of the endoscope were contaminated with a germ suspension which contained the following germs:

1) approx. $10^9$ germs/ml Staphylococcus aureus
2) approx. $10^9$ germs/ml Pseudomonas aeruginosa
3) approx. $10^7$ germs/ml Candida albicans To simulate practical conditions, the germ suspensions contained an addition of 20% by weight defibrinated sheep's blood.

For contamination, the bores of the endoscope were filled with the germ suspension. After brief standing, the germ suspensions were drained off. One hour after contamination, the endoscope was cleaned and disinfected in accordance with the invention. 0.5 liter of a solution containing 3% by weight Tween 80, 0.3% by weight lecithin, 0.1% by weight histidine, 0.1% by weight tryptone and 0.05% by weight sodium chloride was then drawn through the bores of the endoscope. One ml samples of this solution were inoculated onto agar plates which were then incubated for at least 48 hours at 37° C. or for at least 72 hours at 35° C. and subsequently tested for any germ growth present.

It was found that, where the process of the invention was applied, satisfactory cleaning disinfection and freedom from germs was obtained in every case.

In further tests carried out under the same conditions
In further tests carried out under the same conditions as described in the example, it was possible to show that the process of the invention is effective as a disinfectant against contamination by hepatitis B virus and entero viruses such as polio and papova.

We claim:

1. A process for the cleaning and disinfecting surfaces of heat and corrosion sensitive medical instruments with an aqueous cleaning and disinfectant solution which comprises in successive steps:
   a) contacting the surfaces to be cleaned and disinfected with the aqueous detergent and disinfectant solution which contains;
      water having a hardness of 3° to 8° Gh (German hardness);
      at least one low foaming nonionic surfactant;
      at least one proteolytic enzyme;
      at least one complexing agent;
      at least one aldehyde disinfectant selected from the group consisting of formaldehyde and aliphatic dialdehydes containing 2 to 8 carbon atoms;
      at a pH of about 6 to about 8, at a temperature of about 55° to 65° C., for about 1 to about 15 minutes;
   b) rinsing the surfaces at least twice with water having a hardness of 3° to 8° Gh (German hardness), at a temperature of about to 55° to about 65° C. at least in the last rinse cycle; and
   c) drying the surfaces with sterilized air at a temperature of about 40° to about 60° C.

2. The process of claim 1, wherein the detergent and disinfectant solution of step a) contains
   from 0.1 to 1.0 g/liter low foaming surfactant,
   from 0.03 to 0.3 AU/liter proteolytic enzyme,
   from 0.02 to 0.3 g/liter complexing agent and
   from 0.5 to 5 g/liter aldehyde 3. The process of claim 1 wherein the detergent and disinfectant solution of step a) contains at least one low foaming nonionic surfactant comprising an alkylene oxide adduct from 3 to 30 mol of at least one member selected from the group consisting of ethylene oxide and propylene oxide to a member selected from the group consisting of aliphatic polyols containing from 2 to 6 hydroxyl groups and from 2 to 12 carbon atoms, fatty alcohols, fatty acids, fatty amines or alkylphenols each containing from 8 to 18 carbon atoms, wherein the terminal groups of the polyglycol ether derivatives can be hydroxyl, etherified hydroxyl, esterified hydroxyl, or acetylated hydroxyl.

4. The process of claim 1 wherein the detergent and disinfectant solution of step a) contains a low foaming nonionic surfactant from the group consisting of adducts of 3 to 15 mol ethylene oxide with saturated and unsaturated $C_8$–$C_{18}$ fatty alcohols, adducts of from 3 to 5 mol ethylene oxide and from 3 to 6 mol propylene oxide with saturated and unsaturated $C_8$–$C_{18}$ fatty alcohols and ether derivatives of the fatty alcohol polyalkylene glycol ethers, in which the terminal hydroxyl groups are etherified with a straight chain or branched chain, saturated aliphatic $C_4$–$C_8$ alcohol.

5. The process of claim 4 wherein the detergent and disinfectant solution of step a) contains as the low foaming surfactant a polyethylene glycol ether of the formula:

$$R^1\text{—}O\text{—}(CH_2CH_2O)_n\text{—}R^2 \qquad (I)$$

in which $R^1$ is a straight chain $C_8$–$C_{18}$ alkyl, a branched chain $C_8$–$C_{18}$ a alkyl, a straight chain $C_8$–$C_{18}$ alkenyl, a branched chain $C_8$–$C_{18}$ a alkenyl, $R^2$ is a straight chain $C_4$–$C_8$ alkyl, a branched chain $C_4$–$C_8$ alkyl radical and n is a number of from 7 to 12.

6. The process of claim 5, wherein the detergent and disinfectant solution of step a) contains a polyethylene glycol ether of formula I in which $R^1$ is a mixture of $C_{12}$–$C_{18}$ radicals of a tallow fatty alcohol and $R^2$ is an n-butyl radical and n is a number of from 9 to 10.

7. The process of claim 1 wherein the detergent and the disinfectant solution of step a) contains at least one complexing agent selected from the group consisting of alkali metal salts of nitrilotriacetic acid, alkali metal salts of ethylenediamine tetracetic acid, alkali metal salts of 1-hydroxyethane-1,1-diphosphonic acid, alkali metal salts of aminotris-(methylene- phosphonic acid), alkali metal salts of ethylenediamine tetrakis-(methylenephosphonic acid), alkali metal salts of phosphonobutane tricarboxylic acid, alkali metal salts of tartaric acid, alkali metal salts of citric acid and alkali metal salts of gluconic acid.

8. The process of claim 7 wherein the detergent and disinfectant solution of step a) contains alkali metal salts of phosphonobutane tricarboxylic acid as complexing agent.

9. The process of claim 1 wherein the detergent and the disinfectant solution of step a) contains glutaraldehyde.

10. The process of claim 1 wherein the medical instrument is an endoscope.

11. The process of claim 10 wherein the endoscope is ultrasonicated in step a).

12. The process of claim 10 wherein the endoscope is treated in step c) with hot air which has been sterilized by passage through a microfilter.

* * * * *